United States Patent [19]
Leushner et al.

[11] Patent Number: 5,830,657
[45] Date of Patent: Nov. 3, 1998

[54] METHOD FOR SINGLE-TUBE SEQUENCING OF NUCLEIC ACID POLYMERS

[75] Inventors: James Leushner, North York; May Hui, West Toronto; James M. Dunn, Scarborough, all of Canada; Marina T. Larson, Yorktown, N.Y.

[73] Assignee: Visible Genetics Inc., Toronto, Canada

[21] Appl. No.: 684,498

[22] Filed: Jul. 19, 1996

Related U.S. Application Data

[63] Continuation-in-part of Ser. No. 640,672, May 1, 1996.
[51] Int. Cl.$^6$ .............................. C12Q 1/68; C12P 19/34; C07H 21/02
[52] U.S. Cl. ............................ 435/6; 435/91.2; 536/24.3
[58] Field of Search ................................... 435/5, 6, 91.1, 435/91.2, 810, 183; 536/24.3

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,729,947 | 3/1988 | Middendorf et al. | 435/6 |
| 4,795,699 | 1/1989 | Tabor et al. | 435/5 |
| 4,889,818 | 12/1989 | Gelfand et al. | 435/194 |
| 4,942,124 | 7/1990 | Church | 435/6 |
| 4,965,188 | 10/1990 | Mullis et al. | 435/6 |
| 5,075,216 | 12/1991 | Innis et al. | 435/6 |
| 5,079,352 | 1/1992 | Gelfand et al. | 538/27 |
| 5,352,600 | 10/1994 | Gelfand et al. | 435/194 |
| 5,427,911 | 6/1995 | Ruano | 435/6 |

FOREIGN PATENT DOCUMENTS

| | | |
|---|---|---|
| 0265293 | 4/1988 | European Pat. Off. . |
| 0386859 | 9/1990 | European Pat. Off. . |
| 0655506 | 5/1995 | European Pat. Off. . |
| 8907149 | 8/1989 | WIPO . |
| 9302212 | 2/1993 | WIPO . |
| 9308305 | 4/1993 | WIPO . |
| 9426894 | 11/1994 | WIPO . |
| 9511961 | 5/1995 | WIPO . |
| 9601909 | 1/1996 | WIPO . |

OTHER PUBLICATIONS

Deng et al., "Simultaneous amplification and sequencing of genomic DNA (SAS) : sequencing of 16s rRNA genes using total genmic DNA from *Butyrovibrio fibrisolvens*, and detection and genotyping of non–cultruable mycoplasma–like organisms directly from total DNA isolated from infected plants", *J. Microbiol.l Methods*17: 103–113 (1993).
Rao, V. B., "Direct–Sequencing of Polymerase Chain Reaction–Amplified DNA", *Anal Biochem*, 216: 1–14 (1994).
Kretz et al., "Cycle Sequencing" in*PCR methods and Applications* 3: S107–S112 (1994).
Tabor et al., "A single residue in DNA polymerase I family is critical for distinguinshin between deoxy and dideoxynucleotides", Proc. Nat 'Acad. Sci. USA. 92: 6339–6343 (1995).
Reeve et al., A novel thermostable polymerase for DNA sequencing *Nature* 376: 796–797 (1995).
Kambara et al, "Real Time Automated Simultaneous Double Stranded DNA Sequencing Using Two–Color Fluorophore Labeling"*Biotechnology* 9: 648–651 (1991).
Sarkar et al., "Dideoxy fingerprinting (ddF) : A rapid and Efficient Screen for the Presence of Mutations" *Genomics* 13: 441–443 (1992).
Wiemann et al., "Simultaneous On–Line Sequencing on Both Strands with Two Fluorescent Dyes" *Anal. Biochem.* 224: 117–121 (1995).
Gyllenstein et al., "Generation of single–stranded DNA by polymerase chain reaction and its application to direct sequencing of the HLA–DQA locus" *Proc. Nat'l Acad. Sci. USA*85: 7652–7656 (1988).
Mullis et al., "Specific Synthesis of DNA in Vitro via a Polymerase–Catalyzed Chain Reaction" *Meth. Enzymol.*155: 335–350 (1987).
Ruano et al., "Genotyping and haplotyping of polymorphisms directly from genomic DNA via coupled amplification and sequencing (CAS)" *Nucl. Acids Res.* 19: 6877–6882 (1991).
Murakawa et al., :Direct Detection of HIV–1 RNA from AIDS and ARC Patient Samples DNA 7: 287–295 (1988).
Carothers et al., "Point Mutation Analysis in A Mammalian Gene: Rapid Preparation of Total RNA, PCR Amplification of cDNA, and Taq Sequencing by Novel Method" *BioTechniques* 7: 494–498 (19.
Murray, V., "Improved Double–Stranded DNA Sequencing Using the Linear Polmerase Chain Reaction", *Nucl. Acids Res.* 17: 8889 (1989).
Sanger et al., "DNA Sequencing with Chain–Terminating Inhibitors", *Proc. Nat'l Acad. Sci.* 74: 5463–5467 (1977).
Miller et al., "Chain Terminator Sequencing of Double–Stranded DNA With Built in Error Correction", General Atomics Pre–Print (1991).
Nuovo, G.J., "In situ PCR" in Dieffenbach et al., *PCR Primer: A Laboratory Manual,*pp. 235–248, Cold Spring Harbor Laboratory Press (1995).
Ruano et al. , "Coupled Amplification and sequencing of geneomic DNA", *Proc. Nat'l Acad. Sci (USA)*88: 2815–2819 (1991).
Ruano et al., "Automated Genomic Coupled Amplification and Sequencing (CAS) of the Mitochondrial D–Loop", Abst. Hilton Head Genomic Analysis Conference (1994). abstract.
Church et al., "Genomic Sequencing"*Proc. Nat'l Acad. Sci.* (USA) 81: 1991–1995 (1984).
Church et al., "The Genomic Sequencing Technique",*Medical Genetics: Past, Present and Future,*pp. 17–21 (1985).

Primary Examiner—Eggerton A. Campbell
Attorney, Agent, or Firm—Oppedahl & Larson

[57] ABSTRACT

Sequencing of a selected region of a target nucleic acid polymer in a genomic DNA sample can be performed in a single vessel by combining the sample with a sequencing mixture containing a primer pair, a thermally stable polymerase such as Thermo Sequenase™ which incorporates dideoxynucleotides into an extending nucleic acid polymer at a rate which is no less than about 0.4 times the rate of incorporation of deoxynucleotides, nucleotide feedstocks, and a chain terminating nucleotide. The mixture is processed through multiple thermal cycles for annealing, extension and denaturation to produce a product mixture which is analyzed by electrophoresis.

8 Claims, 9 Drawing Sheets

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:

( A ) ORGANISM: human ( i x ) FEATURE:
    ( D ) OTHER INFORMATION: amplification primer for DR1 alleles of HLA Class II genes ( x i ) SEQUENCE DESCRIPTION: SEQ ID NO:1:

TTGTGGCAGC TTAAGTTTGA AT      22

( 2 ) INFORMATION FOR SEQ ID NO: 2:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:2:

CCGCCTCTGC TCCAGGAG      18

( 2 ) INFORMATION FOR SEQ ID NO: 3:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:3:

CCCGCTCGTC TTCCAGGAT      19

( 2 ) INFORMATION FOR SEQ ID NO: 4:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
    ( A ) ORGANISM: human ( i x ) FEATURE:
    ( D ) OTHER INFORMATION: amplification primer for DR2 alleles of HLA Class II genes ( x i ) SEQUENCE DESCRIPTION: SEQ ID NO:4:

TCCTGTGGCA GCCTAAGAG 19

( 2 ) INFORMATION FOR SEQ ID NO: 5:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR2 alleles of HLA Class II genes ( x i ) SEQUENCE DESCRIPTION: SEQ ID NO:5:

CCGCGCCTGC TCCAGGAT 18

( 2 ) INFORMATION FOR SEQ ID NO: 6:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR2 alleles of HLA Class II genes ( x i ) SEQUENCE DESCRIPTION: SEQ ID NO:6:

AGGTGTCCAC CGCGCGGCG 19

( 2 ) INFORMATION FOR SEQ ID NO: 7:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid (  i i i ) HYPOTHETICAL:no (  i v ) ANTI-SENSE: yes (  v ) FRAGMENT TYPE: internal (  v i ) ORIGINAL SOURCE:
    ( A ) ORGANISM: human (  i x ) FEATURE:
    ( D ) OTHER INFORMATION: amplification primer for DR3, 8, 11,
        12, 13, 14 alleles of HLA Class II genes (  x i ) SEQUENCE DESCRIPTION: SEQ ID NO:7:

CACGTTTCTT GGAGTACTCT AC 22

( 2 ) INFORMATION FOR SEQ ID NO: 8:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR3, 8, 11,
            12, 13, 14 alleles of HLA Class II genes ( x i ) SEQUENCE DESCRIPTION: SEQ ID NO:8:

CCGCTGCACT GTGAAGCTCT 20

( 2 ) INFORMATION FOR SEQ ID NO: 9:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR4 alleles of
            HLA Class II genes ( x i ) SEQUENCE DESCRIPTION: SEQ ID NO:9:

GTTTCTTGGA GCAGGTTAAA CA 22

( 2 ) INFORMATION FOR SEQ ID NO: 10:

( i ) SEQUENCE CHARACTERISTICS:
        ( A ) LENGTH: 20
        ( B ) TYPE: nucleic acid ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: human ( i x ) FEATURE:
            ( D ) OTHER INFORMATION: amplification primer for DR4 alleles of
                HLA Class II genes ( x i ) SEQUENCE DESCRIPTION: SEQ ID NO:10:

CTGCACTGTG AAGCTCTCAC 20

( 2 ) INFORMATION FOR SEQ ID NO: 11:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: human ( i x ) FEATURE:
            ( D ) OTHER INFORMATION: amplification primer for DR4 alleles of
                HLA Class II genes ( x i ) SEQUENCE DESCRIPTION: SEQ ID NO:11:

CTGCACTGTG AAGCTCTCCA 20

( 2 ) INFORMATION FOR SEQ ID NO: 12:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
            ( A ) ORGANISM: human ( i x ) FEATURE:
            ( D ) OTHER INFORMATION: amplification primer for DR7 alleles of
                HLA Class II genes ( x i ) SEQUENCE DESCRIPTION: SEQ ID NO:12:

CCTGTGGCAG GGTAAGTATA 20

( 2 ) INFORMATION FOR SEQ ID NO: 13:

( i ) SEQUENCE CHARACTERISTICS:
( A ) LENGTH: 21
( B ) TYPE: nucleic acid
( C ) STRANDEDNESS: double
( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
( A ) ORGANISM: human ( i x ) FEATURE:
( D ) OTHER INFORMATION: amplification primer for DR7 alleles of HLA Class II genes ( x i ) SEQUENCE DESCRIPTION: SEQ ID NO:13:

CCCGTAGTTG TGTCTGCACA C 21

( 2 ) INFORMATION FOR SEQ ID NO: 14:

( i ) SEQUENCE CHARACTERISTICS:
( A ) LENGTH: 23
( B ) TYPE: nucleic acid
( C ) STRANDEDNESS: double
( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
( A ) ORGANISM: human ( i x ) FEATURE:
( D ) OTHER INFORMATION: amplification primer for DR9 alleles of HLA Class II genes ( x i ) SEQUENCE DESCRIPTION: SEQ ID NO:14:

GTTTCTTGAA GCAGGATAAG TTT 23

( 2 ) INFORMATION FOR SEQ ID NO: 15:

( i ) SEQUENCE CHARACTERISTICS:
( A ) LENGTH: 21
( B ) TYPE: nucleic acid
( C ) STRANDEDNESS: double
( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
( A ) ORGANISM: human ( i x ) FEATURE:
( D ) OTHER INFORMATION: amplification primer for DR9 alleles of HLA Class II genes ( x i ) SEQUENCE DESCRIPTION: SEQ ID NO:15:

CCCGTAGTTG TGTCTGCACA C                                                                 21

( 2 ) INFORMATION FOR SEQ ID NO: 16:

( i ) SEQUENCE CHARACTERISTICS:
          ( A ) LENGTH: 19
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: amplification primer for DR10 alleles
              of HLA Class II genes ( x i ) SEQUENCE DESCRIPTION: SEQ ID NO:16:

CGGTTGCTGG AAAGACGCG                                                                    19

( 2 ) INFORMATION FOR SEQ ID NO: 17:

( i ) SEQUENCE CHARACTERISTICS:
          ( A ) LENGTH: 20
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( v i ) ORIGINAL SOURCE:
          ( A ) ORGANISM: human ( i x ) FEATURE:
          ( D ) OTHER INFORMATION: amplification primer for DR10 alleles
              of HLA Class II genes ( x i ) SEQUENCE DESCRIPTION: SEQ ID NO:17:

CTGCACTGTG AAGCTCTCAC                                                                   20

( 2 ) INFORMATION FOR SEQ ID NO: 18:

( i ) SEQUENCE CHARACTERISTICS:
          ( A ) LENGTH: 18
          ( B ) TYPE: nucleic acid
          ( C ) STRANDEDNESS: double
          ( D ) TOPOLOGY: linear ( i i ) MOLECULE TYPE: other nucleic acid ( i i i ) HYPOTHETICAL: NO ( i v ) ANTI-SENSE: yes ( v ) FRAGMENT TYPE: internal ( v i ) ORIGINAL SOURCE:
          ( A ) ORGANISM: human ( i x ) FEATURE:
          ( D ) OTHER INFORMATION: amplification primer for VHL exon 2

( x i ) SEQUENCE DESCRIPTION: SEQ ID NO:18:

GGCTCTTTAA CAACCTTT                                                                                              18

( 2 ) INFORMATION FOR SEQ ID NO: 19:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: NO ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for VHL exon 2

( x i ) SEQUENCE DESCRIPTION: SEQ ID NO:19:

GGGCTTAATT TTTCAAGTGG TC                                                                                         22

METHOD FOR SINGLE-TUBE SEQUENCING OF NUCLEIC ACID POLYMERS

SPECIFICATION

This application is a continuation-in-part of U.S. patent application Ser. No. 08/640,672 filed May 1, 1996.

BACKGROUND OF THE INVENTION

This application relates to DNA sequencing reactions, and in particular to improved sequencing reaction protocols making use of thermally stable polymerase enzymes having enhanced capacity to incorporate chain terminating nucleosides during chain termination sequencing reactions.

DNA sequencing is generally performed using techniques based on the "chain termination" method described by Sanger et al., *Proc. Nat'l Acad. Sci.* (USA) 74(12): 5463–5467 (1977). Basically, in this process, DNA to be tested is isolated, rendered single stranded, and placed into four vessels. In each vessel are the necessary components to replicate the DNA strand, i.e., a template-dependant DNA polymerase, a short primer molecule complementary to a known region of the DNA to be sequenced, and individual nucleotide triphosphates in a buffer conducive to hybridization between the primer and the DNA to be sequenced and chain extension of the hybridized primer. In addition, each vessel contains a small quantity of one type of dideoxynucleotide triphosphate, e.g. dideoxyandenosine triphosphate(ddA).

In each vessel, each piece of the isolated DNA is hybridized with a primer. The primers are then extended, one base at a time to form a new nucleic acid polymer complementary to the isolated pieces of DNA. When a dideoxynucleotide is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleic acid in that vessel. These sets of polymers are then evaluated using gel electrophoresis to determine the sequence.

Improvements to the original technique described by Sanger et al. have included improvements to the enzyme used to extend the primer chain. For example, Tabor et al. have described enzymes such as T7 DNA polymerase which have increased processivity, and increased levels of incorporation of dideoxynucleotides. (See U.S. Pat. No. 4,795,699 and EP-A1-0 655 506, which are incorporated herein by reference). More recently, Reeve et al. have described a thermostable enzyme preparation, called THERMO SEQUENASE™, with many of the properties of T7 DNA polymerase. *Nature* 376: 796–797 (1995). The literature supplied with the THERMO SEQUENASE™ product suggests dividing a DNA sample containing 0.5–2 µg of single stranded DNA (or 0.5 to 5 µg of double stranded DNA) into four aliquots, and combining each aliquot with the THERMO SEQUENASE™ enzyme preparation, one dideoxynucleotide termination mixture containing one ddNTP and all four dNTP's; and a dye-labeled primer which will hybridize to the DNA to be sequenced. The mixture is placed in a thermocycler and run for 20–30 cycles of annealing, extension and denaturation to produce measurable amounts of dye-labeled extension products of varying lengths which are then evaluated by gel electrophoresis.

Each of the processes known for determining the sequence of DNA can be preceded by amplification of a selected portion of the genetic material in a sample to enrich the concentration of a region of interest relative to other DNA. For example, it is possible to amplify a selected portion of a gene using a polymerase chain reaction (PCR) as described in U.S. Pat. Nos. 4,683,194, 4,683,195 and 4,683,202, which are incorporated herein by reference. This process involves the use of pairs of primers, one for each strand of the duplex DNA, that will hybridize at a site located near a region of interest in a gene. Chain extension polymerization (without a chain terminating nucleotide) is then carried out in repetitive cycles to increase the number of copies of the region of interest many times. The amplified polynucleotides are then separated from the reaction mixture and used as the starting sample for the sequencing reaction. Gelfand et al. have described a thermostable enzyme, "Taq polymerase," derived from the organism *Thermus aquaticus*, which is useful in this amplification process. (See U.S. Pat. Nos. 5,352,600 and 5,079,352 which are incorporated herein by reference)

U.S. Pat. No. 5,427,911, which is incorporated herein by reference, describes a process for coupled amplification and sequencing of DNA. In this process, a sample is combined with two primers and amplified for a number of cycles to achieve 10,000 to 100,000-fold amplification of the initial geneomic DNA. Thereafter, the sample is divided into 8 test and 2 control aliquots. The test aliquots each receive one type of dideoxynucleotide triphosphates and a labeled primer complementary to one of the amplified DNA strands. Thus, the eight test aliquots taken together provide one reaction for each base type in each sequencing direction.

While the methods now available for DNA sequencing produce useful results, they all involve multiple steps. This makes them reasonably well-suited for use in a research environment, where the sequence of genetic materials is being determined for the first time, but less well-suited for use in a routine diagnostic procedure where the sequence of the same region of DNA is determined over and over again in multiple patients. For this latter purpose, it would be desirable to have a process for the sequencing of genetic materials which could be performed with fewer steps and in a single vessel, and which is therefore more suited to automation. It is the object of the present invention to provide such a method.

SUMMARY OF THE INVENTION

The present invention is based on the observation and discovery that the addition of a reaction mixture containing the thermostable polymerase THERMO SEQUENASE™, two primers which bind to complementary strands of a target DNA molecule at sites flanking a region of interest, a mixture of nucleotide triphosphates (A, C, G and T) and one dideoxynucleotide triphosphate to a genomic DNA sample and the processing of the combination through multiple cycles of annealing, extension and denaturation results in the production of a mixture which can be loaded directly onto a gel for sequence analysis. Thus, one aspect of the present invention is a method for sequencing a selected region of a target nucleic acid polymer comprising the steps of (a) combining a sample containing the target nucleic acid polymer with a reaction mixture comprising all four types of deoxynucleotide triphosphates, one type of dideoxynucleotide triphosphate, first and second primers and a thermally stable polymerase enzyme which incorporates dideoxynucleotides into an extending nucleic acid polymer at a rate which is no less than about 0.4 times the rate of incorporation of deoxynucleotides in an amplification mixture for a plurality of amplification cycles to form a reaction mixture, said first and second primers binding to the sense and antisense strands, respectively, of the target nucleic acid polymer for amplification of the selected region;

(b) exposing the reaction mixture to a plurality of temperature cycles each of which includes at least a high temperature denaturation phase and a lower temperature extension phase to produce a product mixture comprising sequencing fragments which are terminated by incorporation of the dideoxynucleotide; and (c) evaluating product mixture to determine the lengths of the sequencing fragments produced.

DETAILED DESCRIPTION OF THE INVENTION

The method of the invention utilizes the properties of enzymes like THERMO SEQUENASE™, namely the ability to incorporate dideoxynucleotides into an extending polynucleotide at a rate which is no less than about 0.4 times the rate of incorporation of deoxynucleotides, to provide a method for the sequencing of a nucleic acid polymer from a sample in a single set of thermocycling reactions which can be carried out in a single vessel. Thus, the method of the invention is ideally suited for automation.

Figure 1:
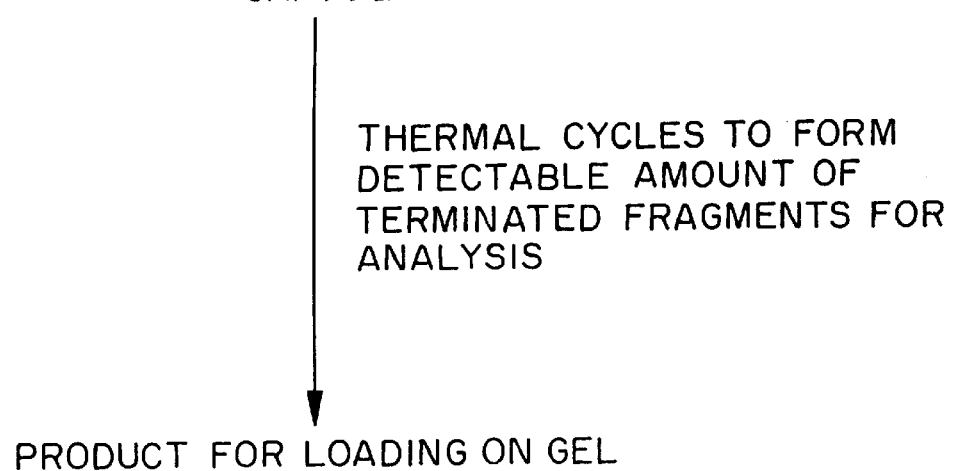
FIG. 1 illustrates the method of the invention schematically.

FIG. 1 illustrates the fundamental simplicity and elegance of the method of the invention in flow chart form. As shown in FIG. 1, a sample containing a target nucleic acid polymer which includes a region to be sequenced is combined with a reaction mixture containing two primers, a mixture of dNTP's, a chain terminating nucleotide, i.e., a dideoxynucleotide triphosphate, and a thermostable polymerase in a buffer suitable for hybridization and template-dependant polymerization. The mixture is processed for a number of thermal cycles sufficient to produce detectable amounts of sequencing fragments, generally from 20 to 50 cycles. The result of this processing is a product mixture containing dideoxy-terminated fragments which can be loaded directly onto an electrophoresis gel for analysis of the sequence.

A key factor in successfully performing the method of the invention is the utilization of THERMO SEQUENASE™ or a comparable enzyme as the thermostable polymerase in the reaction mixture. Such an enzyme is characterized by a high affinity for incorporating dideoxynucleotides into the extending nucleotide chain. Thus, for example, Thermo Sequenase is known to favor the incorporation of dideoxynucleotides. In general, for purposes of the present invention, the polymerase used should be one which incorporates dideoxynucleotides into an extending nucleic acid polymer at a rate which is no less than about 0.4 times the rate of incorporation of deoxynucleotides.

Figure 2A:
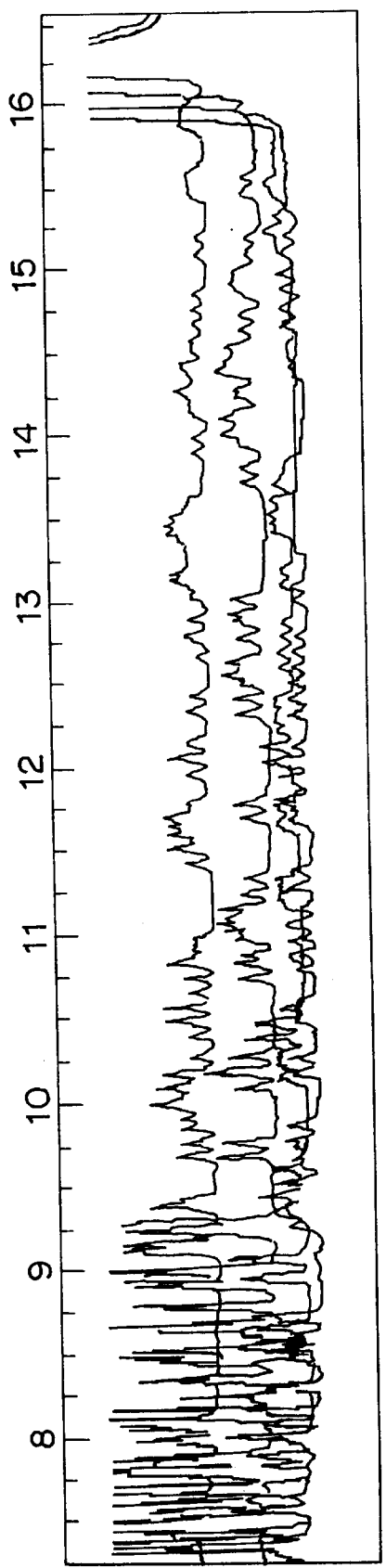
FIGS. 2A–2C show a comparison of sequencing runs performed using THERMO SEQUENASE™ as the polymerase in the method of the invention with results obtained using other thermostable polymerases in comparative experiments.
Figure 2B:
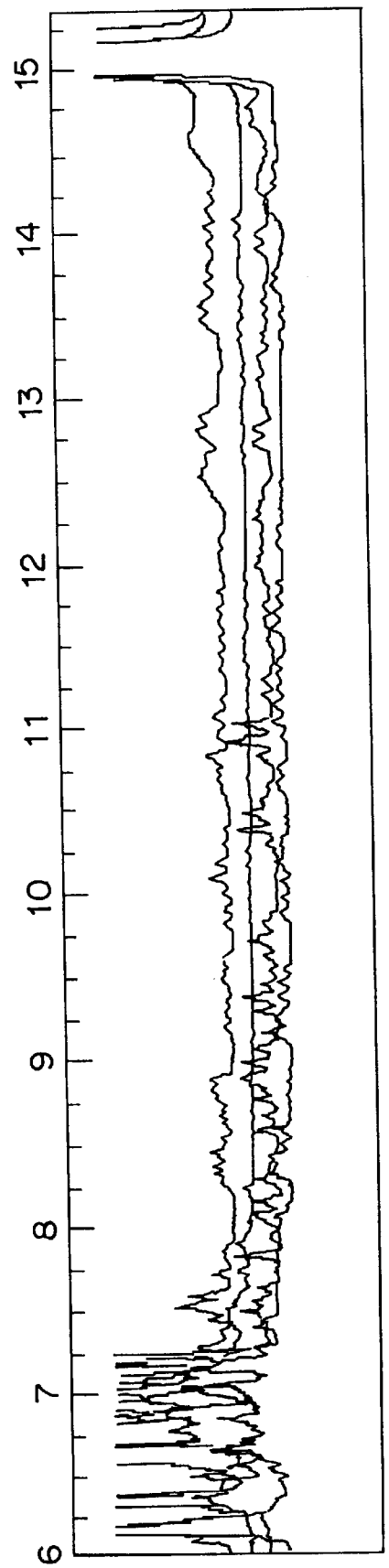
Figure 2C:
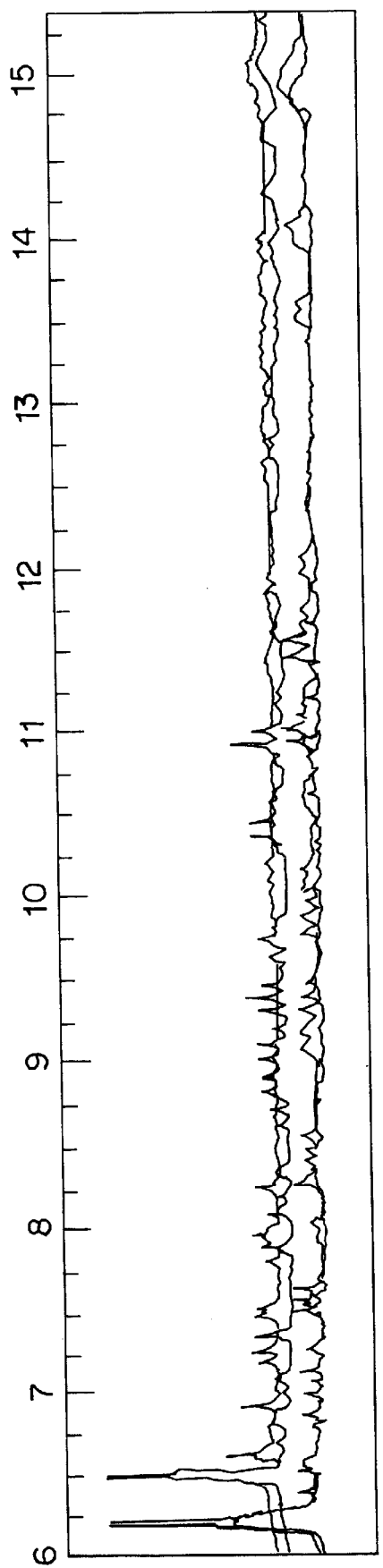
Figure 3:
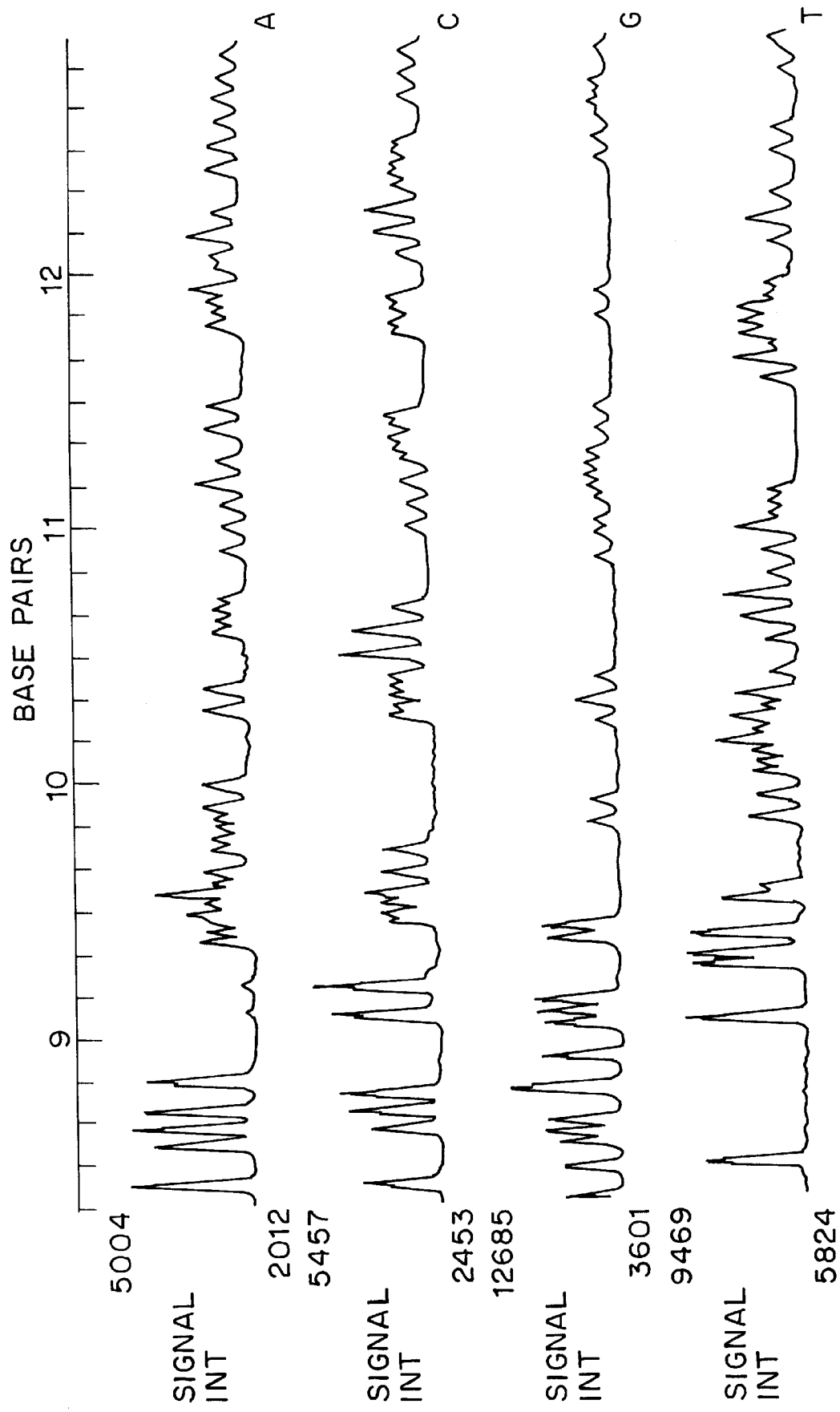
FIG. 3 shows the data trace of FIG. 2A in greater detail.
Figure 4A:
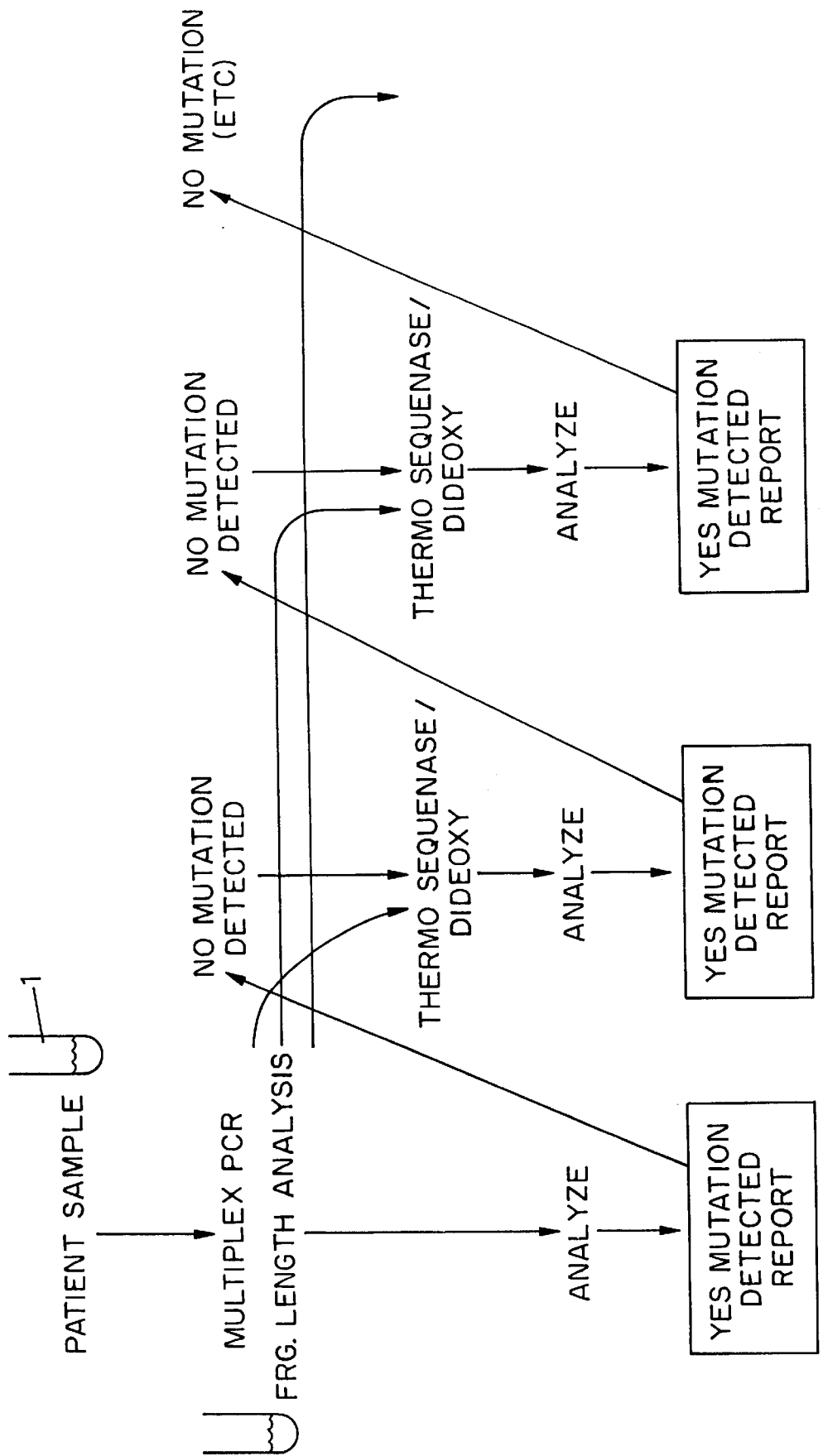
FIGS. 4A and 4B illustrates a diagnostic method which incorporates the amplification and sequencing process of the present invention with a fragment-based analysis.
Figure 4B:
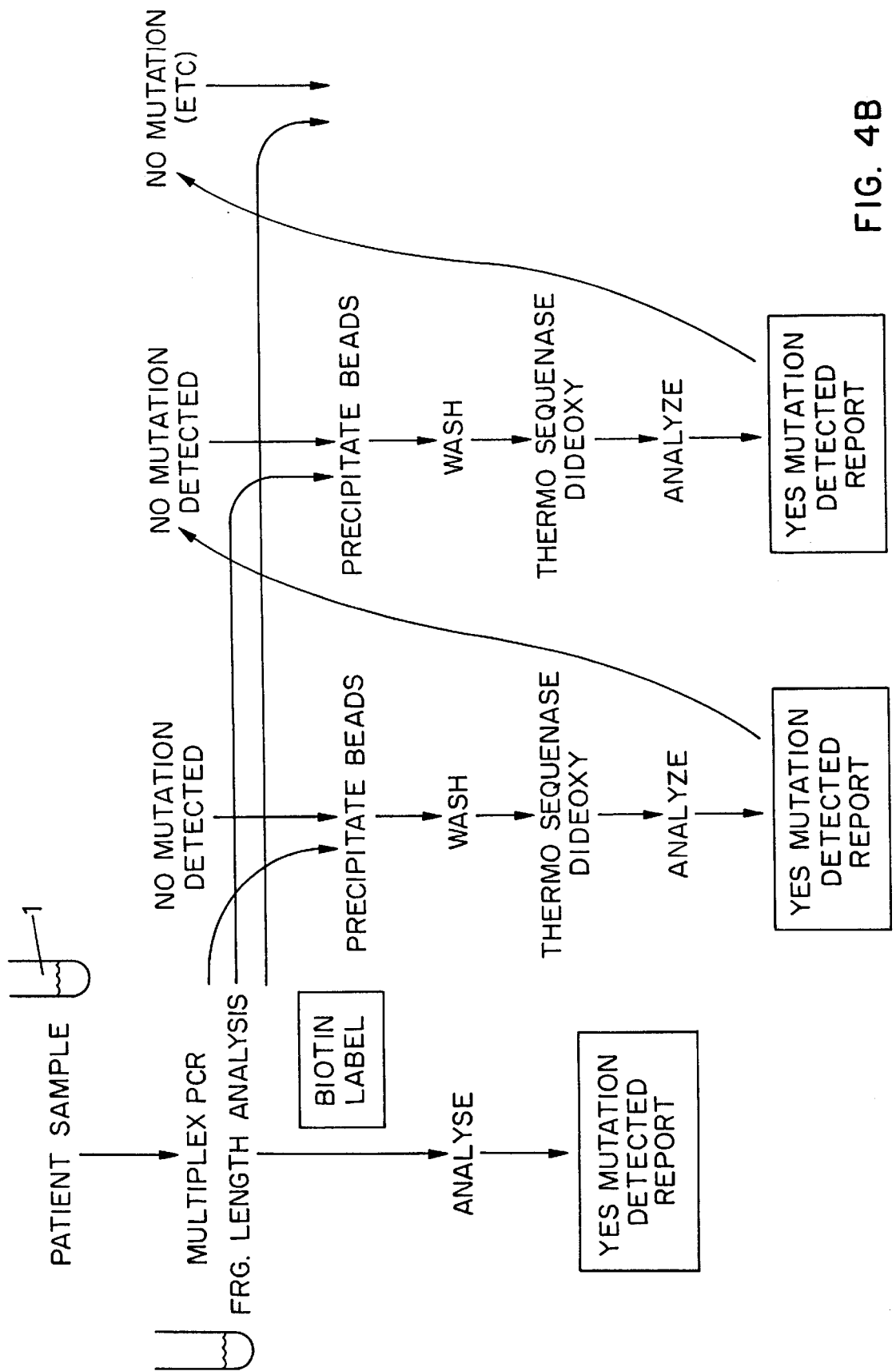
Figure 5:
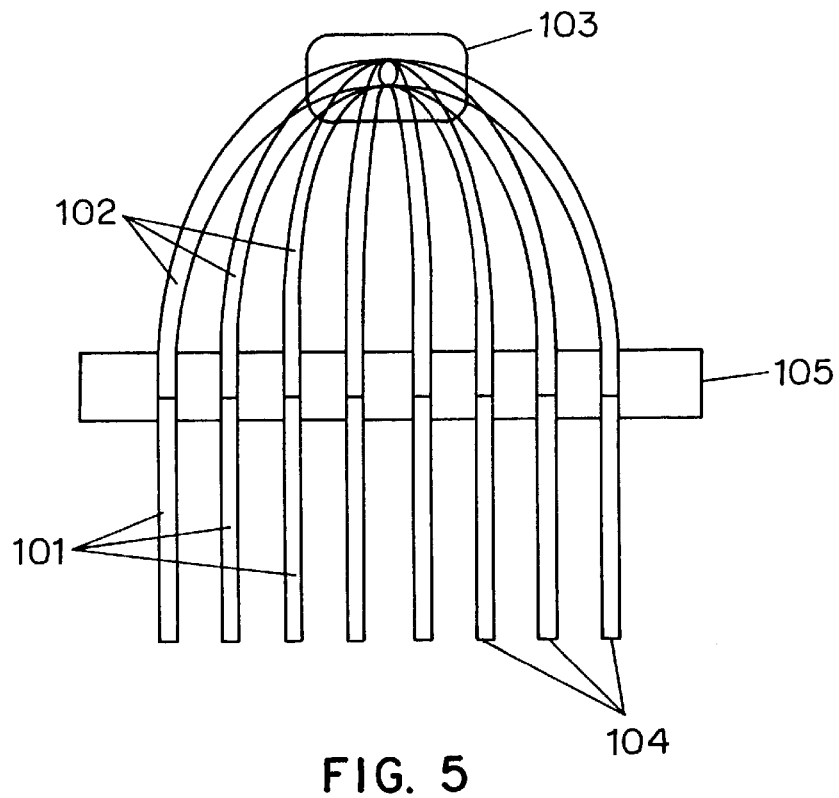
FIG. 5 depicts a portion of an apparatus useful in carrying out the present invention.

FIGS. 2A–2C and FIG. 3 illustrate the importance of this characteristic of the polymerase enzyme employed. FIGS. 2A and 3 shows a sequencing data trace for an actual patient sample of genomic DNA which was obtained using THERMOS SEQUENASE™ and primers effective to amplify exon 2 of the Von Hippel-Lindau gene in a process according to the invention. Large, well-defined peaks corresponding to the termination fragments were obtained which made sequence evaluation of the sample very straightforward. This result was obtained performing the test in a single reaction vessel, with a single unaugmented reaction mixture, in a total of 35 thermal cycles. In contrast, FIG. 2B shows the trace obtained when a combination of Vent and Sequitherm™ were used instead of THERMO SEQUENASE™. In this trace, the peaks for the termination fragments are much smaller and less well defined. Performing the same experiment using Taq polymerase resulted in a data trace that contained no usable peaks.

The operation of the invention can be understood in the context of a hypothetical 200 nt DNA fragment having equal amounts of each base. This means that there will be 50 potential truncation events during the cycle. For each cycle, some of the amplification products would be full length (and thus subject to further amplification) and some would be truncated at the points where the ddNTP was added. If each of these truncation events has a statistical likelihood of occurring 1 time in 500 as a result of the relative concentration of ddNTP compared to dNTP and the relative incorporation by the enzyme, then overall a truncation product will occur in slightly less than ten percent of the reactions. Table 1 shows the relative amounts of amplified and chain-termination products theoretically formed after 10, 20 and 30 cycles of simultaneous amplification and chain-termination reaction of this 200 nt polynucleotide assuming various ratios of truncated to amplified product.

TABLE 1

| Cycles | truncation ratio = 0.1 | | truncation ratio = 0.3 | | truncation ration = 0.5 | |
|---|---|---|---|---|---|---|
| | truncated | amplified | truncated | amplified | truncated | amplified |
| 10 | 32 | 613 | 86 | 202 | 57 | 57 |
| 20 | 41,000 | 376,000 | 17,400 | 40,462 | 3,300 | 3,300 |
| 30 | 25.6 × 10⁶ | 230 × 10⁶ | 3.5 × 10⁶ | 8.2 × 10⁶ | 190,000 | 190,000 |

In actual practice, it has been found that useful results are obtained with Thermo Sequenase™ when the reaction is run for 35 to 45 cycles, using a dideoxy:deoxy mole ratio of 1:100 to 1:300. Thus, in general it can be expected that mole ratios of 1:50 to 1:500 will yield acceptable results. Specific optimum levels for other enzymes found to have the appropriate affinity of incorporating dideoxynucleotides can be identified by routine optimization using the THERMO SEQUENASE™ values as a starting point.

In the present invention, the two primers used function as both an amplification primer and a sequencing primer. Accordingly, at least one of the primers is advantageously labeled with a detectable label such as a radiolabel, a fluorophore, a chromophore, a fluorogenic or chromogenic label, or any other label which can facilitate the detection of the sequencing fragments produced in the reaction. The fact that the primer serves two functions, however, means that full length product (the product spanning from one primer to the other) will also be detected during sequencing and may be a substantial band relative to any of the individual truncation products. To avoid losing information due to the size of this band, it may be advantageous to use a relatively long primer, for example a 20–25 mer such that the difference in length between the full length product and the longest possible truncation product will be 21 to 26 bases.

It may also be advantageous to label both primers used in the method of the invention. For example, the second primer can include a label such as biotin that renders it readily removable from the solution by immobilization on a solid support. In this case, the amount of unlabeled polynucleotide can be substantially reduced, thus improving the performance of the subsequent electrophoresis by adding avidin or streptavidin-coated beads to separate the other strand.

Alternatively, the second primer can be labeled with a second detectable label, preferably different in characteristics from the first label. For example, the primers can be labeled with two different fluorophores as in the process described by Wiemann et al., "Simultaneous On-Line DNA Sequencing on Both Stands with Two Fluorescent Dyes," *Anal. Biochem* 224: 117–121 (1995). Analysis of the fragments labeled with the two different labels can be accomplished by loading aliquots of the reaction mixture onto two different electrophoresis lanes which are evaluated for different label types or by loading the product mixture onto one lane in a multi-dye sequencer which has the ability to evaluate several labels in a single instrument.

It may also be advantageous when possible to select a primer sequence which does not include the base corresponding to the ddNTP of the sequencing reaction to avoid truncations within the primer portion of the product polynucleotide. This means that four separate sets of amplification/sequencing primers may need to be constructed for any one region. This is less burdensome than it might seem, however, since in many cases sequencing of only a single base is sufficient for diagnostic purposes. (See U.S. patent application Ser. No. 08/577,858, which is incorporated herein by reference.

One of the important characteristics of the present invention is the fact that it permits conversion of genomic DNA to a sequencing product mixture in a single set of thermocycling reactions without modification of or addition to the reagents present in the reaction mixture. As used herein, the term "genomic DNA" refers to DNA in which the various portions of the DNA in the sample are present in substantially natural relative abundance. Thus, genomic DNA is DNA which has not been subjected to amplification or cloning to enhance the concentration of one portion of the DNA in the sample relative to other portions. The term "genomic DNA" does not, however, require the presence of all the DNA from the original sample. Thus, a sample containing just nuclear DNA, or just mitochondrial DNA or some subfraction of nuclear or mitochondrial DNA obtained by isolation from a tissue sample but not subjected to preferential amplification would be "genomic DNA" within the meaning of that term in the specification and claims of this application.

Genomic DNA can be prepared from blood or tissue samples by any of a number of techniques, including salt precipitation or standard SDS-proteinase K-phenol extraction. Genomic DNA can also be prepared using kits, for example the Gentra Pure Gene DNA Isolation Kit.

The present invention can also be used on non-genomic DNA (that is DNA which has been previously amplified) and provides very useful sequencing results. FIGS. 3A and 3B illustrate a particularly useful application of the method of the present invention as part of an overall diagnostic strategy in which a series of analytical techniques may be performed on the same sample, depending on the outcome of the initial test. Hierarchical techniques of this type are described in U.S. patent applications Ser. Nos. 08/271,942, 08/271,946, and 08/388,381 which are incorporated herein by reference.

As shown in FIGS. 3 A and 3B, a patient sample 1 is first subjected to multiplex PCR to produce a complex mixture of amplification products. Since many clinically significant conditions, for example mutations in the RB1 gene, may involve deletions which are readily and inexpensively detectable by performing fragment length analysis on this mixture, a first step in many hierarchical analysis will be such a fragment length analysis.

According to the hierarchical model, if the results of the fragment length analysis fail to show a mutation, the sample 1 if further analyzed, for example by sequencing a selected exon. Prior to the present invention, however, this required the individual amplification of the selected exon from the sample because the there was not enough template in the initial multiplex PCR reaction to serve as a sequencing template. Using the method of the present invention, however, an aliquot of the original multiplex PCR amplification mixture can be used as the starting material for the sequencing method of the invention. Thus, the multiplex PCR amplification mixture is combined with two primers (at least one of which is labeled) for the exon to be sequenced, a reaction mixture containing a polymerase such as Thermo Sequenase™, and deoxy and dideoxynucleotide triphosphates and then processed for multiple cycles to produce the sequencing fragment mixture for analysis. Preferably, the multiplex amplification PCR is performed using capturable primers (for example biotin-labeled primers) and separated from the multiplex amplification reagents using affinity beads (e.g. avidin-coated beads) prior to the addition of the amplification/ sequencing reagents. (FIG. 3B). Additional aliquots of the multiplex reaction mixture may be processed to sequence different regions if no mutation is detected in the first sequencing step.

It should be noted that the multiplex reaction performed in the first step of this embodiment makes used of labeled primers. Fluorescence from these primers may interfere with observation of a few peaks in the sequencing ladder. This interference can be minimized by utilizing a nested sequencing primer, which produces fragments having a maximum length which is shorter than the multiplex amplification products, or by the utilization of distinguishable labels for the multiplex amplification and sequencing primers.

Another application for which the method of the invention is well-suited is use in performing in-situ sequencing reactions. In situ PCR reactions have been used as a histological tool for mapping the location of certain DNA sequences within a tissue sample. Basically, as described by G. J. Nuovo in *PCR Primer: A Laboratory Manual,* C. W. Dieffenbach et al, eds., Cold Spring Harbor Laboratory Press, pp. 235–248 (1995), PCR amplification is used to increase the number of copies of a selected DNA sequence in a histological tissue preparation, and then hybridization probes are used to identify the parts of the tissue preparation where the amplified DNA is found. In this way, in-situ PCR increases the sensitivity of the hybridization process.

The method of the invention can be used to produce sequencing fragments in situ which are then removed from a selected location on the tissue preparation and loaded onto a gel for sequence analysis. This approach is particularly useful for evaluation of archived samples in retrospective studies where the outcome of a disease condition is known, but the potentially causative mutation is not. This method can be used with labeled primers for single base sequencing (or multiple-base sequencing using multiple tissue samples) using labeled primers, or for multiple base sequencing using distinctively labeled chain terminating nucleotides.

EXAMPLE 1

A 175 ng sample of genomic DNA prepared from a patient blood sample using the Gentra™ Pure Gene DNA isolation kit. Briefly, in this procedure the blood cells were lysed, centrifuged to recover the lysed white blood cells and mixed with proteinase K. Protein is then separated from the sample by precipitation and the remaining nucleic acids are precipitated and collected. The resulting genomic DNA preparation was combined with two primers effective to amplify exon 2 of the VHL gene.
5' primer—labeled with the fluorophore Cy5;
GGCTCTTTAA CAACCTTT [SEQ ID No.: 18]
3' primer—unlabeled;
GGGCTTAATT TTTCAAGTGG TC [SEQ ID No.: 19]
The reaction mixture employed had the following composition:

|  |  |  | final amt. | final vol. |
|---|---|---|---|---|
| DNA genomic |  |  | 175 ng | 3.5 ul |
| 5' Primer | 1 pM/ul |  | 3 pMol | 3.0 ul |
| 3' Primer) | 7.5 pM/ul |  | 23 pMol | 3.0 ul |
| DMSO | 100% |  |  | 1.5 ul |
| THERMO SEQUENASE ™ Reaction Buffer |  |  |  | 2.0 ul |
| THERMO SEQUENASE ™ Enzyme | 32 U/ul |  | 6.4 U | 0.2 ul |
| Total |  |  |  | 13.2 ul |

3 ul aliquots of the reaction mixture were placed into each of 4 tubes containing 3 ul of one of the following termination mixes: A,C,G or T (dNTP/ddNTP; 100:1 ratio; 750 microM: 7.5 microM)after which the mixture was layered with oil.

The mixture was then processed in PTC 100 Thermocycler at follows:
denature
95° 120 sec
35 cycles
95° 50 sec
52° 30 sec
70° 60 sec
finish
70° 120 sec
6° soak
6 ul dye/stop solution was then added to each tube to a final volume of 12 ul. A 2 ul sample was then loaded onto a thin polyacrylamide gel and analyzed in a MICROGENE BLASTER™ sequencer (Visible Genetics Inc, Toronto, Canada). The result was a clean, easily interpreted sequencing ladder.

EXAMPLE 2

A 500 ng sample of genomic DNA prepared from a patient sample using a standard SDS-Proteinase K-phenol extraction was combined with the same two primers as in Example 1 for amplification of exon 2 of the VHL gene. The reaction mixture employed had the following composition:

|  |  | final amt. | final vol. |
|---|---|---|---|
| DNA genomic |  | 500 ng | 1.0 ul |
| 5' Primer) | 3 pMol |  | 3.0 ul |
| 3' Primer | 3 pMol |  | 3.0 ul |
| DMSO | 100% |  | 1.5 ul |
| THERMO SEQUENASE ™ Reaction Buffer |  |  | 2.0 ul |
| THERMO SEQUENASE ™ Enzyme | 32 U/ul | 6.4 U | 0.2 ul |
| distilled water |  |  | 3.0 ul |
| Total Volume |  |  | 13.2 ul |

3 ul aliquots of the reaction mixture were placed into each of 4 tubes containing 3 ul of one of the following termination mixes: A, C, G or T (dNTP/ddNTP; 100:1 ratio; 750 microM: 7.5 microM) after which the mixture was layered with oil.

The mixture was then processed in PTC 100 Thermocycler at follows:
denature
94° 120 sec
45 cycles
94° 20 sec
52° 20 sec
72° 20 sec
finish
72° 150 sec
6° soak
6 ul dye/stop solution was then added to each tube to a final volume of 12 ul. A 1 ul sample was then loaded onto a thin polyacrylamide gel and analyzed in a MICROGENE BLASTER™ Sequencer (Visible Genetics Inc, Toronto, Canada).

For comparison, a sample of the same genomic DNA was treated in a similar reaction using a mixture of Vent Enzyme and SEQUITHERM™ Enzyme as follows:

|  |  | final amt. | final vol. |
|---|---|---|---|
| DNA genomic |  | 1 ug | 8.0 ul |
| 5' Primer (Cy5.5 labeled) |  | 12.5 pMol | 12.5 ul |
| 3' Primer (unlabeled) |  | 12.5 pMol | 12.5 ul |
| Triton X-100 | 20% |  | 25 ul |
| 1 mM each dNTP |  |  | 4.0 ul |
| 10X Vent Buffer |  |  | 5.0 ul |
| 10X SEQUITHERM ™ Buffer |  |  | 5.0 ul |
| Vent Enzyme | 2 U/ul |  | 2.0 ul |
| Sequithem Enzyme | 5 U/ul |  | 2.0 ul |
| distilled water |  |  | 6.5 ul |
| Total Volume |  |  | 82.5 ul |

20 ul of reaction mixture of aliquoted into each of 4 tubes containing 5 ul of one of the following ddNTP in water:
ddATP: 850 uM
ddCTP: 500 uM
ddGTP: 100 uM
ddTTP: 1700 uM
and layered with oil. These mixtures were processed in a PTC 100 thermocycler as follows:
denature
94° 90 sec
45 cycles 94° 20 sec
52° 20 sec
72° 20 sec
finish
72° 150 sec
6° soak 25 ul of dye/stop solution as then added to each tube to a final volume of 50 ul. 2 ul aliquots of this solution were loaded onto a MICROGENE BLASTER™ sequencer for analysis.

A further comparison example was performed using the same patient sample and first amplifying it for 19 cycles under standard PCR conditions, i.e., 94° 2 minutes
19 cycles
94° 50 sec
52° 30 sec
70° 60 sec
finish
70° 150 sec prior to addition of the sample to the VENT/SEQUITHERM™ reaction mixture.

The sequencing traces taken for these three experiments are shown in FIGS. 2A–2C and 3. FIGS. 2A and FIG. 3 which shows the result for the THERMO SEQUENASE™ runs according to the invention is vastly superior to the comparative tests even though a smaller volume of initial DNA and a smaller number of cycles were used. Thus, these experiments demonstrate the surprising characteristics of the method of the invention.

EXAMPLE 3

For comparison to the method of the invention, an experiment was conducted in which the ability of Taq Polymerase to produce usable sequencing fragments directly from genomic DNA was tested. No sequence information could be obtained using Taq polymerase.

EXAMPLE 4

Identification of HLA Class II gene alleles present in an individual patient sample can be performed using the method of the instant invention. For example, DRB1 is a polymorphic HLA Class II gene with at least 107 known alleles (See Bodmer et al. Nomenclature for Factors of the HLA System, 1994. Hum. Imm. 41, 1–20 (1994)).

The broad serological subtype of the patient sample DRB1 allele is first determined by attempting to amplify the allele using group specific primers.

Genomic DNA is prepared from the patient sample using a standard technique such as proteinase K proteolysis. Allele amplification is carried out in Class II PCR buffer:

10 mM Tris pH 8.4

50 mM KCl 1.5 mM MgCl2

0.1% gelatin 200 microM each of dATP, dCTP, dGTP and dTTP 12 pmol of each group specific primer 40 ng patient sample genomic DNA Groups are amplified separately. The group specific primers employed are:

|  |  |  | PRODUCT SIZE |
|---|---|---|---|
| DR 1 |  |  |  |
| 5'-PRIMER: | TTGTGGCAGCTTAAGTTTGAAT | [Seq ID No. 1] | 195 & 196 |
| 3'-PRIMERS: | CCGCCTCTGCTCCAGGAG | [Seq ID No. 2] |  |
|  | CCCGCTCGTCTTCCAGGAT | [Seq ID No. 3] |  |
| DR2, 15 and 16 |  |  |  |
| 5'-PRIMER: | TCCTGTGGCAGCCTAAGAG | [Seq ID No. 4] | 197 & 213 |
| 3'-PRIMERS: | CCGCGCCTGCTCCAGGAT | [Seq ID No. 5] |  |
|  | AGGTGTCCACCGCGCGGCG | [Seq ID No. 6] |  |
| DR3,8,11,12,13,14 |  |  |  |
| 5'-PRIMER: | CACGTTTCTTGGAGTACTCTAC | [Seq ID No. 7] | 270 |
| 3'-PRIMER: | CCGCTGCACTGTGAAGCTCT | [Seq ID No. 8] |  |
| DR4 |  |  |  |
| 5'-PRIMER: | GTTTCTTGGAGCAGGTTAAACA | [Seq ID No. 9] | 260 |
| 3'-PRIMERS: | CTGCACTGTGAAGCTCTCAC | [Seq ID No. 10] |  |
|  | CTGCACTGTGAAGCTCTCCA | [Seq ID No. 11] |  |
| DR7 |  |  |  |
| 5'-PRIMER: | CCTGTGGCAGGGTAAGTATA | [Seq ID No. 12] | 232 |
| 3'-PRIMER: | CCCGTAGTTGTGTCTGCACAC | [Seq ID No. 13] |  |
| DR9 |  |  |  |
| 5'-PRIMER: | GTTTCTTGAAGCAGGATAAGTTT | [Seq ID No. 14] | 236 |
| 3'-PRIMER: | CCCGTAGTTGTGTCTGCACAC | [Seq ID No. 15] |  |
| DR10 |  |  |  |
| 5'-PRIMER: | CGGTTGCTGGAAAGACGCG | [Seq ID No. 16] | 204 |
| 3'-PRIMER: | CTGCACTGTGAAGCTCTCAC | [Seq ID No. 17] |  |

The 5'-primers of the above groups are terminally labeled with a fluorophore such as a fluorescein dye at the 5'-end.

The reaction mixture is mixed well. 2.5 units Taq Polymerase are added and mixed immediately prior to thermotion cycling. The reaction tubes are placed in a Robocycler Gradient 96 (Stratagene, Inc.) and subject to thermal cycling as follows:

1 cycle 94° C. 2 min
10 cycles 94° C. 15 sec
 67° C. 1 min
20 cycles 94° C. 10 sec
 61° C. 50 sec
 72° C. 39 sec
1 cycle 72° C. 2 min
 4® C cool on ice until ready for electrophoretic analysis.

Seven reactions (one for each group specific primer set) are performed. After amplification 2 microl of each of the PCR products are pooled, and mixed with 11 microl of loading buffer consisting of 100% formamide with 5 mg/ml dextran blue. The products are run on a 6% polyacrylamide electrophoresis gel in an automated fluorescence detection apparatus such as the Pharmacia A.L.F.™ (Uppsala, Sweden). Size determinations are performed based on migration distances of known size fragments. The serological group is identified by the length of the successfully amplified fragment. Only one fragment will appear if both alleles belong to the same serological group, otherwise, for heterozygotes containing alleles from two different groups, two fragments appear.

Once the serological group is determined, specificity within the group is determined by single nucleotide sequencing according to the invention of U.S. patent application Ser. No. 08/577,858.

Each positive group from above is individually combined with a pair of primers, at least one of which includes a detectable label. Suitable primer pairs are made up of a 5'-primer selected from those described above and a 3'-primer:

5' CCGCTGCACTGTGAAGCTCT 3' [Seq ID No. 8]

The conditions for generation of the sequencing products are the same as those described in Example 1 or 2 using Thermo Sequenase™ or another enzyme having a high affinity for incorporation of dideoxynucleotides. After cycling add 12 ul of loading buffer consisting of 100% formamide with 5 mg/ml dextran blue, and load appropriate volume to an automated DNA sequencing apparatus, such as a Pharmacia A.L.F. or a Visible Genetics MICROGENE BLASTER™.

The various embodiments of the invention described above provide the ability to produce sequencing fragments directly from a genomic DNA sample in a single reaction vessel. As noted above, in many cases of clinical significance it may be sufficient to determine the position of just one base within a target nucleic acid polymer in the sample. In this case, the complete diagnostic process can be completed in a single vessel, thus greatly simplifying the requirements of the process for automation. When explicit determination of all four bases is considered necessary, the process can be carried out in four separate tubes, one for each sequencing reaction. These tubes may all incorporate a single dye to label the sequencing primers, in which case the products of each reaction are loaded onto a separate lane of a sequencing gel; or the tubes may each incorporate a distinct fluorescent label, in which case the sequencing reaction products may be combined prior to loading onto a multi-dye instrument.

The sequencing reactions in accordance with the invention are advantageously carried out in an apparatus which is automated to perform both the sample preparation and the thermocycling steps. FIGS. 5–8 depict an apparatus suitable for this purpose.

In the apparatus of FIGS. 5–8, a plurality of capillary tubes 101, open at both ends, are used as the reaction vessels. The capillaries 101 are held by a support 105 to permit transport as a group between a sample preparation zone 210 and a thermal cycling zone 211 within the apparatus. Capillary tube 101 is typically made of glass or another inert substance. It preferably has an inside diameter of about 1.1 mm, such as Fisher-brand™ or Pyrexbrand™ capillaries sold by Fisher Scientific (Ottawa, Canada).

The capillaries 101 are connected to a sensitive two way pump 103 either directly or by way of tubing 102. A single pump 103 may be used for all capillaries, or each capillary may have its own dedicated pump. When pump 103 is operated the open end of capillary tip 104 withdraws or expels liquid as programmed. Pump 103 is preferably a piston displacement pump with linear actuators. The motor of pump 103 must have sufficient torque to drive the linear actuator, while having sufficient sensitivity to allow precise measurements of very small liquid samples. The Drummond Nanoject™ pump (Cat No. 3-00-203-X, Drummond Scientific Co., Broomall, Pa.) is sensitive to measure nanolitres of fluid is appropriate for use in the apparatus.

The support 105 is positioned in a robotic apparatus 200 which provides X, Y, and Z displacement of the support 105 relative to sample preparation trays 201 and an integrated thermal cycling chamber 202. The position of support 105 and the associated capillaries 101 is controlled by the programming of robotic apparatus 200. A programmable controller is present, though not shown. Many types of robotic apparatus are currently employed in the art, as exemplified by the existing commercial sample preparation apparatuses. Programmable robots position capillary tip 104 in a reagent well 203 and then activate pump 103 to draw liquid into capillary 101. The robot then removes capillary tip 104 from the well and moves it to another position.

A plurality of trays 201, each of which may hold a microtiter plate or other container for holding reagents and/or samples for analysis, are disposed within the dimensional parameters of the X, Y, and Z axes of the robot, as indicated. Trays 201 are temperature controlled for preparation of reactants.

Wells 203 of microtiter plate 201 are loaded with reagents for selected thermal cycling reactions, for example: reagents for PCR amplification; reagents for DNA sequencing and stop reagents such as formamide and visible dye, used for inhibiting enzyme action. The addition of reagents to microtiter plate 201 may be done by a commercially available automated sample preparation instrument.

Figure 7:
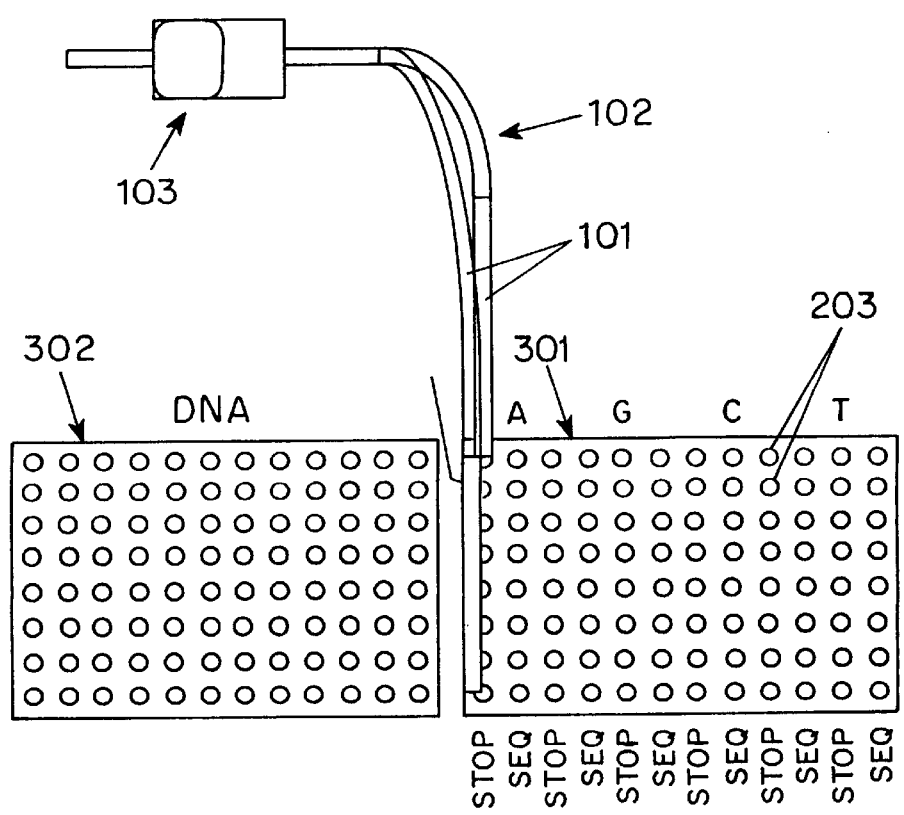
FIG. 7 depicts a portion of an apparatus useful in carrying out the present invention.
Figure 6:
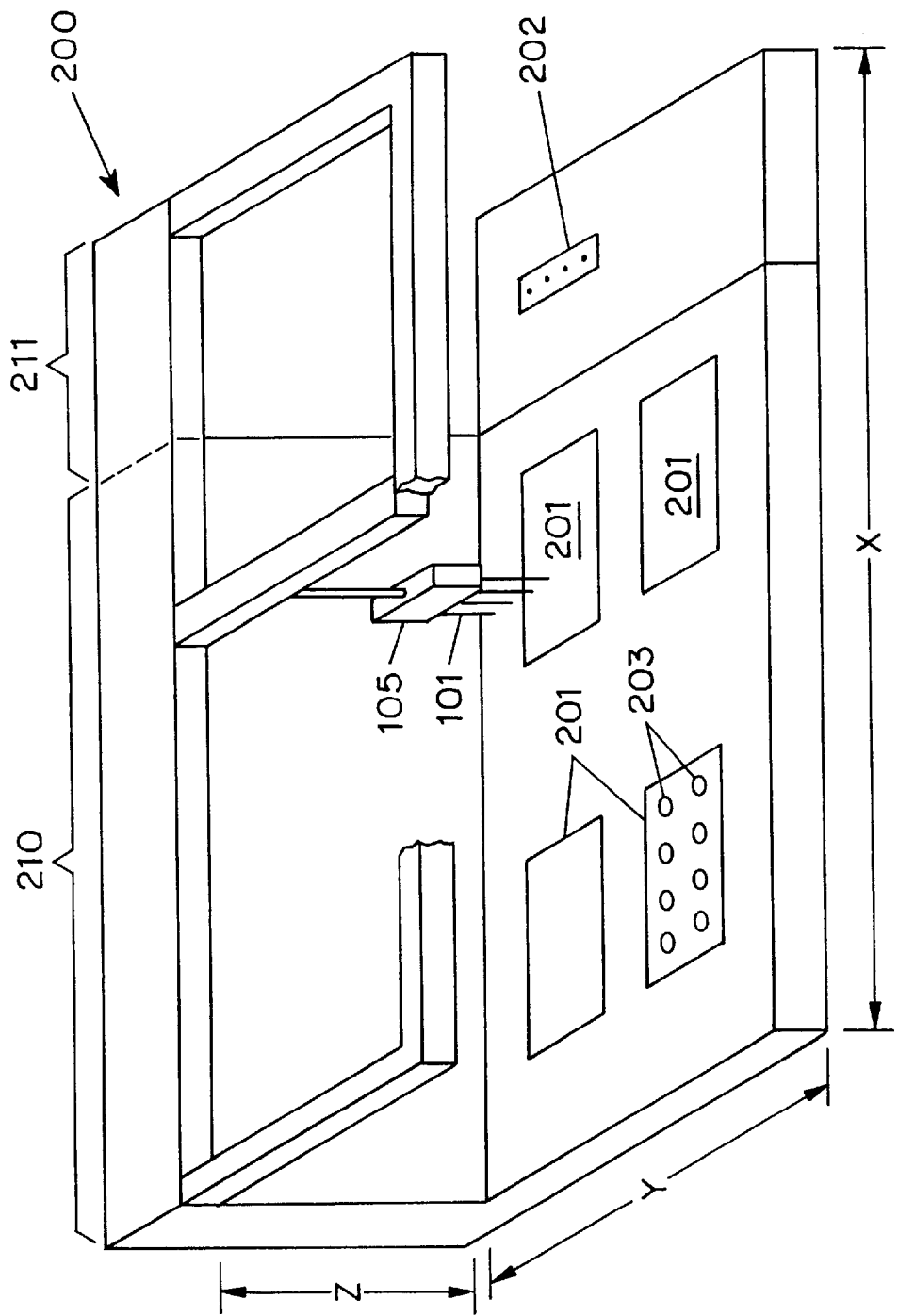
FIG. 6 depicts a robotic apparatus useful in carrying out the present invention.

Reagents are positioned in the wells 203 a fashion convenient for sequential utilization as shown in FIG. 7. Reagents for nucleic acid sample preparation are present in reagent plate 301. As shown, sequencing reaction mixture and stop solution are present in alternating columns of wells 203. A separate microtiter plate 302 is loaded with sample DNA to be tested. The plate is kept at 4 degrees C. during the preparation period.

To carry out the method of the present invention, fresh capillaries 101 dips into DNA samples to be tested in microtiter plate 302. A series of 8 or 12 capillaries is most suitable for use with standard microtiter plates. Pump 103 draws an aliquot of DNA from plate 302 into the capillary 101. Capillary tip 104 is removed by the positional robot and inserted into sequencing reagent wells in plate 301. These wells generally include all the reaction components required for the sequencing reaction of the sample DNA, although two or more wells can be used to provide the reagents for one reaction if desired.

The DNA sample is expelled into wells of plate 301 containing PCR reaction mixture and fully drawn up and down two or more times to mix. Finally, an appropriate reaction volume (e.g. 2 microliters) of mixture is drawn into capillary 101, capillary tip 104 is removed from the well and the mixture is drawn up the capillary approximately 2 cm. The positioning robot then moves capillary 101 to the thermal cycling zone 211.

Within the thermocycling zone 211 of the apparatus is a thermocycling chamber 202 which contains a sealing device for reversibly sealing the capillaries 101. As shown FIG. 8, sealing mechanism 400 is provided to reversibly seal a capillary having a reaction mixture therein. Sealing mechanism 400 has a conformable sealing surface 402 against which the available open ends of a row of capillary tubes can be placed flush, thereby sealing them. Sealing surface 402 is made of a chemically inert elastic substance which must be sufficiently deformable to match the imperfections of capillary tip 104, e.g., rubber or neoprene. Sealing surface 402 is suitably sterile to prevent contamination of samples. Further, a transport system can be provided, for example in the form of a supply roll 403 and uptake roll 403', to provide a fresh sealing surface for each successive application of the capillary or capillaries.

Loaded capillary 401 is placed into thermal cycler 202, and capillary tip 104 is pressed snugly against sealing surface 402. When pressing tip 104 into sealing surface 402, the positional controller robot directs its force directly along the axis of the capillary and does not deflect from this axis, in order to limit breakage of capillaries. The sealing mechanism is preferably of small size in order to minimize the thermal mass. It is preferably located entirely within the sample compartment.

Once sealed, air pressure from the pump is increased. The air pressure in the capillary is maintained higher than the vapor pressure of the sample to prevent solution from escaping, especially during the high temperature period of the thermal cycles. The air pressure may be increased and fixed prior to the thermal cycling. Alternatively, the air pressure may be dynamic during the course of the thermal cycles and increase or decrease as preferred. Some changes of air pressure inside the reversibly sealed capillary will also result from the temperature changes during thermal cycling. Sealing surface 402, therefore, must also be sufficiently rigid to contain the increased air pressure in the capillary.

Figure 8:
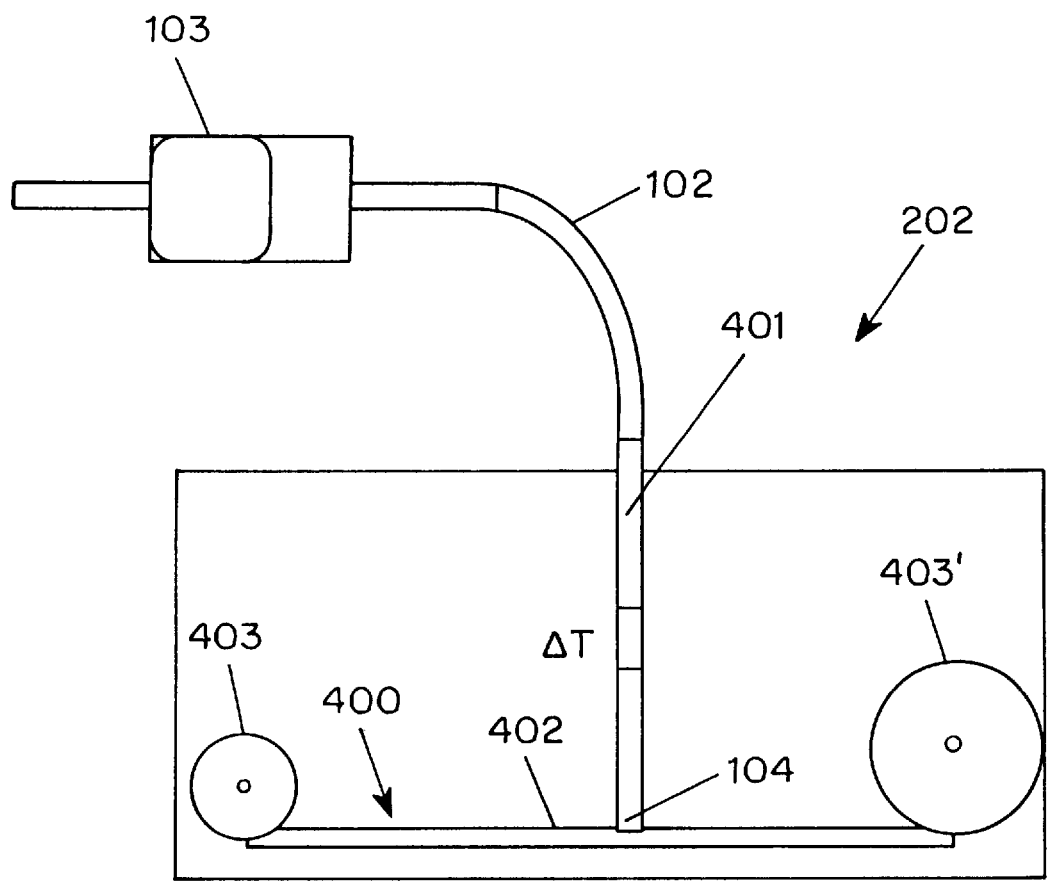
FIG. 8 depicts a side cross-sectional view of a thermocycling device having a reversible sealing mechanism useful in carrying out the present invention.

Although a single capillary 401 is depicted in FIG. 8, it is understood that a row of capillaries having reaction mixture may be treated as described. Multiple capillaries may be sealed and undergo thermal cycling by contacting them with the sealing surface at the same time.

Once sealed, capillaries are then subjected to thermal cycling by introducing successive waves of heated air or other heat conducting gas or fluid. Thermal heat cycles will generally be similar to those disclosed in Examples 1 and 2 above, although variations in the specific temperatures and times, as well as the number of cycles are well within the skill of the art.

After the appropriate number of thermal cycles, the reaction mixture is brought to room temperature or below and the air pressure inside the capillary is returned to standard. The air-tight seal is broken by removing the contact between the capillaries and the plug. This is automatically accomplished by the robotic arm moving the capillaries away from the plug. The capillaries are removed from the thermal cycler by means of the robotic arm and returned to the sample preparation zone 210.

After the sequencing reactions, the tip 104 of each capillary 101 is placed in a stop solution and transferred for loading on an electrophoresis gel.

The present invention makes it very easy to design sequencing kits for the detection of mutations in genes of medical significance. In the past, a kit for carrying out an analysis on a genomic DNA sample required one set of amplification primers (generally unlabeled), and a separate labeled sequencing primer. As a consequence of using the method of the invention, however, one can provide only a single tube of reactants for each portion of the genomic DNA to be sequenced (for example one tube per exon). Thus, a further aspect of the present invention are kits for sequencing a plurality of DNA regions from a genomic DNA sample consisting of a single region-specific reagent for each region, and optionally one or more non-region-specific reagents. For a single use kit, the single region specific reagent will generally be packaged in just one container, although it will be understood that proving multiple containers of the same reagent is within the scope of the present invention.

We claim:

1. A method for sequencing of a selected region of a target nucleic acid polymer in a sample containing the selected region in substantially natural relative abundance, comprising the steps of:

(a) combining the sample containing the target region in substantially natural relative abundance with first and second primers, a nucleotide triphosphate feedstock mixture, a chain-terminating nucleotide triphosphate and a thermally stable polymerase enzyme which incorporates dideoxynucleotides into an extending nucleic acid polymer at a rate which is no less than 0.4 times the rate of incorporation of deoxynucleotides in an amplification mixture to form a reaction mixture, said first and second primers binding to the sense and antisense strands, respectively, of the target nucleic acid polymer at locations flanking the selected region;

(b) exposing the reaction mixture to a plurality of temperature cycles each of which includes at least a high temperature denaturation phase and a lower temperature extension phase, thereby producing a plurality of terminated fragments; and (c) evaluating terminated fragments produced during the additional cycles to determine the sequence of the selected region, wherein at least one of the first and second primers is labeled with a fluorescent label.

2. The method of claim 1, wherein the polymerase enzyme is THERMO SEQUENASE™.

3. The method of claim 1, wherein the first and second primers are each labeled with a different fluorescent label.

4. The method of claim 1, wherein the mole ratio of the dideoxynucleotide triphosphate to the corresponding deoxynucleotide triphosphate is from 1:50 to 1:500.

5. The method of claim 1, wherein the mole ratio of the dideoxynucleotide triphosphate to the corresponding deoxynucleotide triphosphate is from 1:100 to 1:300.

6. A kit for sequencing a plurality of DNA regions from a genomic DNA sample consisting of, in packaged combination, a single region-specific reagent for each DNA region, and optionally one or more non-region-specific reagents.

7. The kit according to claim 6, wherein the kit includes a polymerase enzyme which incorporates dideoxynucleotides into an extending nucleic acid polymer at a rate which is no less than 0.4 times the rate of incorporation of deoxynucleotides.

8. The kit according to claim 7, wherein the polymerase enzyme in THERMO SEQUENASE™.

* * * * *